US005741881A

United States Patent [19]

Patnaik

[11] Patent Number: 5,741,881
[45] Date of Patent: Apr. 21, 1998

[54] PROCESS FOR PREPARING COVALENTLY BOUND-HEPARIN CONTAINING POLYURETHANE-PEO-HEPARIN COATING COMPOSITIONS

[75] Inventor: Birendra K. Patnaik, Chester, N.J.

[73] Assignee: Meadox Medicals, Inc., Oakland, N.J.

[21] Appl. No.: 755,190

[22] Filed: Nov. 25, 1996

[51] Int. Cl.$^6$ .................................................. C08G 18/62
[52] U.S. Cl. .......................... 528/75; 525/453; 525/460; 536/21; 514/56; 530/380; 128/DIG. 22
[58] Field of Search .................... 528/75; 525/453, 525/460; 536/21; 514/56; 530/380; 128/DIG. 22

[56] References Cited

U.S. PATENT DOCUMENTS

| | | | |
|---|---|---|---|
| 4,229,838 | 10/1980 | Mano | 427/2 |
| 4,331,697 | 5/1982 | Kudo et al. | 427/2 |
| 4,521,564 | 6/1985 | Solomon et al. | 525/54.1 |
| 4,600,652 | 7/1986 | Solomon et al. | 428/423.3 |
| 4,613,517 | 9/1986 | Williams et al. | 427/2 |
| 4,642,242 | 2/1987 | Solomon et al. | 427/2 |
| 4,678,660 | 7/1987 | McGary et al. | 424/25 |
| 4,713,402 | 12/1987 | Solomon | 523/112 |
| 4,720,512 | 1/1988 | Hu et al. | 523/112 |
| 4,786,556 | 11/1988 | Hu et al. | 428/412 |
| 4,973,493 | 11/1990 | Guire | 427/2 |
| 4,979,959 | 12/1990 | Guire | 623/66 |
| 5,028,597 | 7/1991 | Kodama et al. | 514/56 |
| 5,061,777 | 10/1991 | Yoda et al. | 528/61 |
| 5,077,352 | 12/1991 | Elton | 525/409 |
| 5,077,372 | 12/1991 | Hu et al. | 528/70 |
| 5,132,108 | 7/1992 | Narayanan et al. | 424/422 |
| 5,134,192 | 7/1992 | Feijen et al. | 523/112 |
| 5,171,264 | 12/1992 | Merrill | 623/3 |
| 5,244,564 | 9/1993 | Narayanan | 424/78.17 |
| 5,258,041 | 11/1993 | Guire et al. | 623/66 |
| 5,409,696 | 4/1995 | Narayanan et al. | 424/422 |
| 5,451,424 | 9/1995 | Solomon et al. | 604/265 |

OTHER PUBLICATIONS

Heparin Immobilization Onto Segmented Polyurethaneurea Surfaces–Effect of Hydrophilic Spacers, by Ki Dong Park, Teruo Okano, Chisato Nojiri, and Sung Wan Kim, Journal of Biomedical Materials Research, vol. 22, 977–992 (1988).

SPUU–PEO–Heparin Graft Copolymer Surfaces: Patentcy and Platelet Deposition in Canine Small Diameter Arterial Grafts by Won Gon Kim, Ki Dong Park, Syed F. Mohammad and Sung Wan Kim; ASAIO Trans 37: M148–M149 (1991).

Synthesis and Characterization of SPUU–PEO–Heparin Graft Copolymers, by Ki Dong Park, Al Zhi Piao, Harvey Jacobs, Teruo Okano and Sung Wan Dim, Journal of Polymer Science: Part A: Polymer Chemistry; vol. 29, 1725–1737 (1991).

PEO–Modified Surfaces–In Vitro, Ex Vivo, and In Vivo Blood Compatibility by Ki Dong Park and Sung Wan Kim in Poly(Ethylene Glycol) Chemistry: Biotechnical and Biomedical Applications, 283–301 (1992).

In Vivo Nonthrombogenicity of Heparin Immobilized Polymer Surfaces by Chisato Nojiri, Ki Dong Park, David W. Grainger, Harvey A. Jacobs, Teruo Okano, Hitoshi Koyanagi and Sung Wan Kim; ASAIO Trans 36: M168–M172 (1990).

Primary Examiner—Rachel Gorr
Attorney, Agent, or Firm—Hoffman & Baron, LLP

[57] ABSTRACT

A bio-active coating composition is described which is the reaction product of two different reactions. The first reaction includes reacting a bio-compatible polymer backbone having $\alpha,\beta$-unsaturated carbonyl functionality with a hydrophilic spacer having at least one reactive functional group at its first and second ends. In this reaction, one of the reactive functional groups of the spacer reacts with a $\beta$-carbon of the carbonyl functionality to bond the spacer to the polymer backbone. The second reaction includes reacting a bio-active agent with a remaining unreacted reactive functional group of the spacer in the presence of an optional catalyst to covalently bind the bio-active agent to the spacer.

44 Claims, No Drawings

PROCESS FOR PREPARING COVALENTLY BOUND-HEPARIN CONTAINING POLYURETHANE-PEO-HEPARIN COATING COMPOSITIONS

FIELD OF INVENTION

The present invention relates generally to bio-active coating compositions. More particularly, the present invention relates to improved bio-active coatings with polymer backbones having $\alpha,\beta$-unsaturated carbonyl functionality therewithin. Bio-active agents are attached to these backbones via spacer groups which bind to the $\beta$-carbon of the $\alpha,\beta$-unsaturated-carbonyl-functionality-containing backbones.

BACKGROUND OF THE INVENTION

It is well known to use bio-active materials to coat structures to be introduced into a living system. Over the last 30 years, research into this area has become increasingly important with the development of various bio-compatible substrates for use in contact with blood, such as, for example, vascular grafts, artificial organs, endoscopes, cannulas, and the like.

While various materials have been used to make such substrates, synthetic polymers have been increasingly popular as the preferred materials due to their anti-thrombogenic and good mechanical properties. For example, polyurethane is a useful and effective material with a variety of clinical applications. Although synthetic polymers, such as, PTFE and polyurethane, are less thrombogenic than earlier materials, thrombus formation is still a problem. A thrombus is the formation of a solid body composed of elements of the blood, e.g., platelets, fibrin, red blood cells, and leukocytes. Thrombus formation is caused by blood coagulation and platelet adhesion to, and platelet activation on, foreign substances. Thus, thrombus formation is a serious complication in surgery and clinical application of artificial organs.

Various anti-thrombogenic agents, such as, heparin, have been developed and incorporated-into bio-compatible substrates to combat thrombus formation. In a living system, heparin inhibits the conversion of a pro-enzyme (prothrombin) to its active form (thrombin). Thrombin catalyzes a complicated biochemical cascade which ultimately leads to the formation of a thrombus.

Infection is also a serious concern for substrates to be implanted into a host organism. Bacterial, viral and other forms of infection may lead to life-threatening complications when a substrate is implanted into a host organism. Thus, binding of an anti-infection agent to a surface of an implantable substrate can reduce the risk of infection when a substrate is introduced into a host organism.

The art is replete with various procedures for grafting bio-active molecules onto polymer surfaces to prevent thrombus formation and/or infection. For example, bio-compatible polymer surfaces have been described with various benefits including decreased thrombogenicity, increased abrasion-resistance and improved hydrophilic lubricious properties. Alternatively, preparing polymeric surfaces to receive bio-active agents by plasma treatment is also well known in the art.

Furthermore, polymer coatings are described that include either covalently or ionically binding bio-active agents to substrate surfaces. For example, as discussed hereinbelow, photochemical reactions are described which covalently bind bio-active agents to substrate surfaces. Also, quaternary ammonium reagents are described which ionically bind a bio-active agent to a substrate.

Alternatively, various substrate surfaces have previously been described that are suitable for introducing into a biological system without pretreatment of any bio-active agent. For example, Yoda et al. in U.S. Pat. No. 5,061,777 disclose that polyurethanes and polyurethaneureas containing both hydrophilic and hydrophobic polyether segments are more anti-thrombogenic than substrates produced from either a hydrophilic or a hydrophobic polyol exclusively. Similarly, Elton in U.S. Pat. No. 5,077,352 discloses a method of forming a mixture of an isocyanate, a polyol and a poly(ethylene oxide) in a carrier liquid. This mixture is then heated and cured to form a coating of a polyurethane complexed with a poly(ethylene oxide) having good adherence to a substrate and good anti-friction properties.

A significant limitation of these bio-compatible polymer surfaces, however, is that they are not completely bio-compatible. Thrombus formation and infection continue to pose problems when a substrate is implanted within a host using these bio-compatible polymer surfaces. Thus, various alternative methods have been described for preparing the surface of a substrate to be implanted in a host organism to accept bio-active agents. Plasma treatment of substrate surfaces is one such method.

For example, Hu et al. in U.S. Pat. No. 4,720,512 disclose a method for imparting improved anti-thrombogenic activity to a polymeric support structure by coating it with an amine-rich material, e.g., a polyurethaneurea, introducing hydrophobic groups into the amine-rich surface coating through plasma treatment with fluorine compounds, and covalently bonding an anti-thrombogenic agent to the hydrophobic amine-rich surface.

Such a method for plasma treating a substrate surface is limited in its scope because it only works with certain substrates. Thus, it does not provide a general purpose coating composition that can bind to a variety of substrate surfaces. In an alternate approach, however, various methods have been described for binding bio-active agents directly to substrate surfaces.

For example, Solomon et al. in U.S. Pat. No. 4,642,242 disclose a process for imparting anti-thrombogenic activity to a polyurethane polymer material by coating a support structure with a protonated amine-rich polyurethaneurea, activating the amine moiety with an alkaline buffer, and covalently linking an anti-thrombogenic agent, e.g., heparin, to the polyurethaneurea with a reducing agent.

Bio-active agents bound directly to polymer backbones suffer from several limitations. First, because these bio-active agents are directly linked to the polymer backbone, their in vivo mobility is decreased. Second, the process of linking the bio-active agent to the polymer backbone may diminish the number of functional binding sites on the bio-active agent. Third, the bio-active agent's close proximity to the polymer backbone limits its ability to interact with its physiological substrates. Thus, for all of these reasons, coatings containing bio-active molecules bound directly to the polymer backbone are limited by the bio-active agent's decreased activity.

Accordingly, alternative methods have been developed for binding bio-active molecules to substrate surfaces. In particular, methods for ionically binding bio-active agents to a substrate via a quaternary ammonium compound have been described. See for example, Mano in U.S. Pat. No. 4,229,838, Williams et al. in U.S. Pat. No. 4,613,517, McGary et al. in U.S. Pat. No. 4,678,660, Solomon et al. in U.S. Pat. No. 4,713,402, and Solomon et al. in U.S. Pat. No. 5,451,424.

These methods, however, are severely limited because the bio-active agent is leached over time from the surface of the substrate. Thus, the protection afforded by the ionically bound bio-active agent to the substrate surface is transient at best. Accordingly, more permanent methods for binding bio-active molecules to substrate surfaces have also been developed. These methods include covalently binding a bio-active molecule, either directly, or via a spacer molecule, to a substrate surface.

For example, photochemical reactions have been described for preparing substrate surfaces to receive anti-thrombogenic agents. Kudo et al. in U.S. Pat. No. 4,331,697 disclose a method for imparting anti-thrombogenic activity to a biomedical material by directly linking a heparin derivative to the surface of the material via actinic radiation. Similarly, Kudo et al. also disclose coating a surface of a biomedical material with a polymer having a carboxylic acid halide group and/or a carboxylic anhydride functional group as a side chain that can react with a heparin derivative.

Alternatively, Guire et al. in U.S. Pat. Nos. 4,973,493 and 4,979,959 disclose methods for binding bio-active molecules to substrates using a linking moiety with functionalized end groups that are preferably activated by different signals. The linking moiety can covalently bind a bio-active molecule upon introduction of a first activation signal which activates the first functionalized end group. The linking moiety is further capable of covalently binding to the substrate upon introduction of a second, different, signal (photochemical) which activates the second functionalized end group.

Bichon et al. in U.S. Pat. No. 4,987,181 disclose a substrate having an adhesive film with anti-thrombogenic properties on its surface. This adhesive film is an olefinic copolymer having side groups distributed randomly on the main chain, wherein these side groups are carboxylic groups and groups of the formula —CONH—(CH$_2$)$_n$—NH—CH$_2$—R, wherein R is a heparin molecule or a depolymerization fragment of a heparin molecule. The adhesive film is deposited onto the substrate via photo-initiated polymerization of a suitable monomer. Thus, heparin, or a fragment thereof, is covalently linked to the substrate via an amine spacer.

Thus, various spacer molecules that link bio-active agents to polymer substrates have been described by the above-referenced studies. These studies indicate that bio-active agents, such as, for example, heparin bound to polymer coatings, retain more of their activity if they are tethered away from the surface of a substrate by a spacer. Although spacer molecules provide a means for optimizing the bio-activity of bio-active molecules bound to substrate surfaces, several problems persist in the photochemical reactions used to bind these bio-active molecules via spacers to substrate surfaces. Included among these problems are the ability of the bio-active molecule to withstand the photochemical signal used to bind it to the substrate surface, as well as the ability of the substrate to withstand photoradiation. For example, inert polymeric substrates, e.g., polytetrafluoroethylene, degrade when exposed to photochemical reactions and cannot be used therewith. Thus, attempts have been made to use spacer molecules to bind bio-active agents to substrate surfaces without photochemical reactive groups.

For example, Park et al. developed a new soluble segmented polyetherurethaneurea-poly(ethylene oxide)-Heparin graft copolymer with improved blood compatibility.

In particular, the new soluble graft copolymer composition is derived from a four step process, wherein heparin is immobilized onto a commercial preparation of a segmented polyetherurethaneurea (PUU) using hydrophilic poly (ethylene oxide) (PEO) spacers of different molecular weights. This new method includes (1) coupling hexamethyldiisocyanate (HMDI) to a segmented polyetherurethaneurea backbone through an allophanate/biuret reaction between the urethane/urea-nitrogen proton and one of the isocyanate groups on the HMDI. Next, (2) the free isocyanate groups attached to the backbone are then coupled to a terminal hydroxyl group on a PEO to form a PUU-PEO product. Next (3) the free hydroxyl groups of the PUU-PEO product are treated with HMDI to introduce a terminal isocyanate group. Finally, (4) the NCO functionalized PUU-PEO is then covalently bonded to reactive functional groups on heparin (—OH and —NH$_2$) producing a PUU-PEO-Hep product. K. D. Park and S. W. Kim, "PEO-Modified Surfaces-In Vitro, Ex Vivo and In Vivo Blood Compatibility", in Poly(Ethylene Glycol) Chemistry: Biotechnical and Biomedical Applications 283, 293–295 (J. Milton Harris ed. 1992). This method will be referred to hereinafter as the "Park Method."

The Park Method suffers from several draw backs. In particular, because of the number of reactions steps involved in the Park Method, the synthesis of the coating composition is slow, inefficient and prone to side reactions which contributes to a low yield and an increase in the amount of cross-linked polymer.

In general, all of these disclosures have addressed substrate surfaces and/or coatings therefor which can exist within biological systems and in particular, can increase the anti-thrombogenicity of the surface of, e.g., medical substrates. These reactions, however, are generally slow, multi-step syntheses, and are characterized by side reactions which lead to low yields and formation of cross-linked polymers. In addition, these reactions cannot be universally applied to substrate surfaces. Thus, in particular, there is a need for a bio-active coating and process that can be used with a broad spectrum of substrate surfaces. In addition, there is a need particularly for bio-active coating compositions that have $\alpha,\beta$-unsaturated functionality as a platform for binding bio-active agents to polymer backbones. There is also a need for a simplified method of preparing such bio-active coatings that provides higher yields with negligible cross-linking, in a shorter period of time. The present invention is directed toward providing a solutions therefor.

SUMMARY OF THE INVENTION

The present invention relates to a bio-active coating composition that is the reaction product of two different reactions. The first reaction includes reacting a bio-compatible polymer backbone having $\alpha,\beta$-unsaturated carbonyl functionality with a hydrophilic spacer having at least one reactive functional group at its first and second ends. In this reaction, one of the reactive functional groups of the spacer reacts with a $\beta$-carbon of the carbonyl functionality to bond the spacer to the polymer backbone. The second reaction includes reacting a bio-active agent with a remaining unreacted reactive functional group of the spacer to covalently bind the bio-active agent to the spacer.

In another embodiment of the present invention, a coating composition is provided which includes a polymeric structure defined by a bio-compatible polymeric backbone having a carbonyl functionality and at least one pendant moiety bonded to a $\beta$-carbon of the carbonyl functionality. The pendant moiety is selected from the group consisting of:

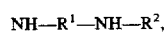

wherein R¹ is a hydrophilic spacer group selected from the group consisting of aliphatic hydrocarbons, poly(oxy olefins) hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides; and R² is a bio-active agent selected from the group consisting of antithrombogenic agents, antibiotics, antibacterial agents, antiviral agents, their pharmaceutical salts and mixtures thereof.

In yet another embodiment of the present invention, there is provided a method for preparing a bio-active polymer coating having a bio-active group covalently bonded through a spacer group to a polymer backbone. This method includes providing a polymer backbone having α,β-unsaturated carbonyl functionality therewithin; reacting a β-carbon of the carbonyl functionality with a hydrophilic spacer having at least one reactive functional group at its first and second ends to attach the hydrophilic spacer as a pendant group off of the backbone; and further reacting the pendant group with a bio-active agent to covalently bond the bio-active agent to the pendant group.

In a further embodiment of the present invention, there is provided a polymer-bound bio-active composition represented by the structure:

wherein P is a biocompatible polymer backbone having a β-carbon derived from an α,β unsaturated carbonyl functionality. R¹ is a hydrophilic spacer group having at least one reactive functional group at its first and second ends and is further selected from the group consisting of aliphatic hydrocarbons, poly(oxy olefins) hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides. R² is a bio-active agent selected from the group consisting of antithrombogenic agents, antibiotics, antibacterial agents, antiviral agents, their pharmaceutical salts and mixtures thereof.

Still further, there is provided a bio-active coating composition which is formed from a polymer backbone with α,β-unsaturated carbonyl functionality. The polymer backbone is formed from four reactions. In the first reaction, a poly diol is reacted with a methylene diisocyanate to form a NCO-terminated prepolymer. In the second reaction, an α,β-unsaturated carbonyl functionality is reacted with the NCO terminated prepolymer to form the polymer backbone. In the third reaction, the polymer backbone is reacted with a hydrophilic spacer group having at least one reactive functionality at its first and second ends. In the fourth reaction, a bio-active agent is reacted with an unreacted end of the hydrophilic spacer in the presence of an optional catalyst to covalently bond the bio-active agent to the polymer backbone via the hydrophilic spacer.

DETAILED DESCRIPTION OF THE INVENTION

While this invention is satisfied by embodiments in many different forms, there will be described herein in detail preferred embodiments of the invention, with the understanding that the present disclosure is to be considered as exemplary of the principles of the invention and is not intended to limit the invention to the embodiments illustrated and described. The scope of the invention will be measured by the appended claims and their equivalents.

In accordance with the present invention, novel bio-active coatings are provided. More particularly, novel compositions and methods are provided for the synthesis of heparinized polyurethanes.

The bio-active coatings and method described herein are particularly advantageous over previously disclosed polymer coatings, especially the Park Method described hereinabove because the α,β-unsaturated carbonyl functionality of the polymer backbones of the present coatings provide more controlled and reproducible bio-active coatings. In addition, the properties of the bio-active coatings of the present invention can be varied easily, e.g., biostability, hydrophilicity etc. Also, the use of α,β-unsaturated carbonyl functionality in the present bio-active coatings increases the reaction efficiencies and reduces the reaction times in comparison to previously disclosed methods. Furthermore, the use of α,β-unsaturated carbonyl functionality in the backbone of the present coatings allows these reactions to be carried out at lower temperatures. Importantly, the α,β-unsaturated carbonyl functionality in the present backbones reduces the number of cross-links formed and provides higher polymer yields than previously described methods. Moreover, these bio-compatible α,β-unsaturated carbonyl functionality-containing polyurethane backbones are not commercially available and are described for the first time herein in connection with the present coatings.

In one embodiment of the present invention, there is provided a bio-active coating composition having a polymer backbone with α,β-unsaturated carbonyl functionality. This coating composition includes four reactions. The first reaction includes reacting a poly diol, such as for example polycarbonate (PC) diol with a diisocyanate functionality (II). Although the preferred polycarbonate diol (I) is described, any poly(diol) may be used that is reactive with the diisocyanate functionality to form an NCO-terminated prepolymer. Other poly(diols) include, for example, polyether(diol) and polyester(diol). Thus, as indicated below RM #1 illustrates the synthesis of prepolymer (III) from a polycarbonate(diol) and a methylene diisocyanate.

Reaction Mechanism (RM) #1

I.　　　　II.

HO—PC—OH + OCN-φ-CH₂-φ-NCO ——→

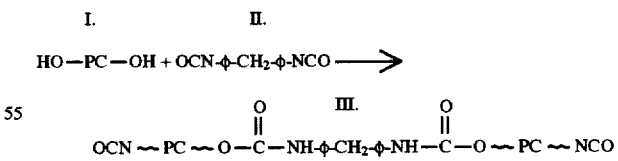

wherein, φ is an aromatic compound having, for example, six carbon atoms. As described above, in RM #1, the diisocyanate functionality is methylene diisocyanate, however, any diisocyanate may be used which is reactive with poly(diol) (I) to form the prepolymer (III).

In RM #1, the resulting NCO-terminated prepolymer (III) is then reacted with an α,β-unsaturated carbonyl functionality, such as for example composition (IV) as described below in RM #2:

RM#2

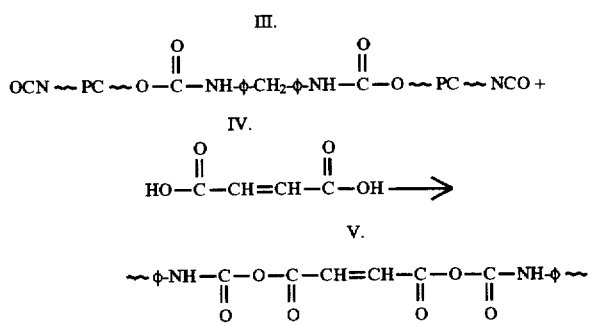

Composition (IV) can be any, α,β-unsaturated carbonyl functionality that is reactive with the prepolymer (III) to form intermediate (V).

Intermediate V is then heated to a temperature sufficient to cause $CO_2$ to be removed from the polymer backbone as indicated below in RM #3. This temperature is below about 100° C. and preferably about 60° C.

RM #3

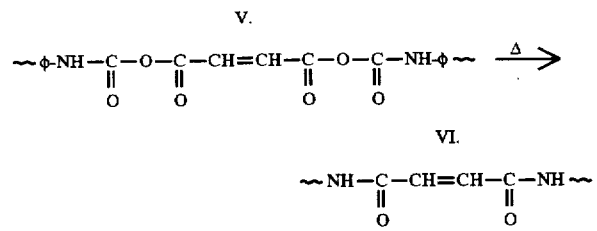

The bio-compatible polymer backbone (VI) of the present invention may be any polymer backbone capable of entering into the reactions described herein. Preferred polymer backbones are polyurethanes including for example, polycarbonateurethaneureas, polyetherurethaneureas, and polyesterurethaneureas. The type of backbone will of course vary according to use, desired properties of the end product, as well as, the starting materials used to synthesize the backbone.

Polymer backbone (VI) is then reacted with a hydrophilic spacer group $R^1$, such as poly(ethylene)oxide (PEO) having at least one reactive functionality at its first, and second ends as indicated below in RM #4:

RM #4

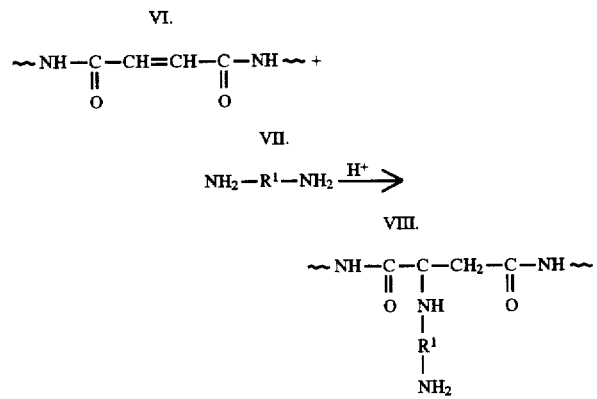

The α,β-unsaturated carbonyl functionality contained within the bio-compatible polymer backbone is selected to participate in Michael addition-type reactions for bonding the spacer to the bio-compatible backbones. Thus, the incorporated carbonyl functionalities of the present polymer backbones include such α,β-unsaturated carbonyl functionalities which are reactive with the spacer and can bond the spacer to the backbone via the β-carbon of the carbonyl functionality. An example of such a carbonyl functionality is HOOC—CH=CH—COOH.

The above indicated reaction, i.e., RM #4, may take place in the presence of a hydrogen donating compound. Preferably, this hydrogen donating compound is an acid. More particularly, this acid is, for example, methanol or dilute fumaric acid.

Although the preferred hydrophilic spacer group, i.e., an me-terminated polyethylene oxide (PEO) spacer, is described, any spacer may be used which is reactive with the β-carbon of the α,β-unsaturated carbonyl functionality in the polymer backbone, as well as, a bio-active agent as described below in RM #5:

RM #5

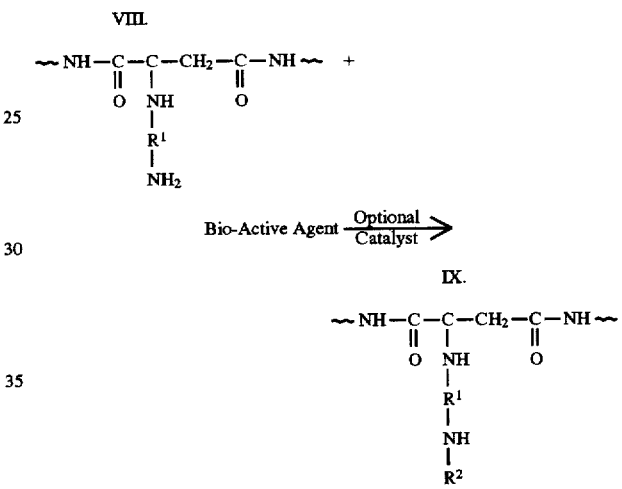

wherein $R^1$ is a spacer group and $R^2$ is a bio-active agent.

In RM #5 described above, a bio-active agent, such as for example heparin is covalently bound to the intermediate (VIII) in the presence of an optional catalyst/dehydrating agent, such as, for example 1-(3-dimethylaminopropyl)-3-ethylcarbodiimide hydrochloride (EDC). In non-aqueous organic solvents, many carbodiimides can be used, such as for example dicyclohexyl carbodiimide. Alternatively, the intermediate VIII can be reacted with an aldehyde terminated heparin, e.g., a nitrous acid degraded heparin molecule.

The product (IX) of RM #5 indicated above is characterized by the chemical linkage, i.e., —NH—, between the spacer and the bio-active molecule, e.g., heparin, as well as between the polymer backbone and the spacer. This composition and its method of synthesis will be referred to hereinafter as "Inventive Embodiment I."

Inventive Embodiment I significantly improves upon previously described bio-active coating compositions and methods of making same, such as the Park Method described hereinabove. In particular, the method of the present invention provides for approximately a 100% increase in polymer yield, while significantly decreasing the amount of polymer cross-linking, i.e. unwanted side-reactions and cross-reactions, and without sacrificing heparin bio-activity.

The bio-active agent of the present invention is bound to the polymer backbone via a spacer group. The spacer group may include poly(oxy olefins) (e.g., poly(ethylene oxide)), aliphatic polyesters, polyamino acids, polyamines, hydrophilic polysiloxanes, hydrophilic polysilazanes, hydrophilic acrylates, hydrophilic methacrylates, and linear or lightly branched polysaccharides. The spacer group is intended to be hydrophilic in order to take advantage of the natural repulsive forces of the hydrophobic polymeric substrate. The spacer group should have reactive functional groups on each end that are capable of reacting with and binding to the bio-compatible polymer backbone and bio-active agent, respectively. Preferably, the reactive functional group on each end of the spacer is, for example, an amine group. As stated above, an amino end-blocked poly(ethylene oxide) is a preferred example.

Moreover, hydrophilic poly(ethylene oxide) spacers are preferred because they have low interfacial free energy, lack binding sites, and exhibit highly dynamic motion. These characteristics are important because they increase the activity of a PEO-linked bio-active agent, e.g., heparin. See, K. D. Park et al., supra.

As previously described, the length of the spacer group may be used to control the bio-active agent's activity. It is known in the art that the anti-thrombogenic activity of heparin is increased when it is positioned a certain distance from the substrate to which it is bound. For example, in a comparison of polymeric substrate-spacer-heparin coatings using a $C_6$ alkyl spacer, PEO 200, PEO 1000 and PEO 4000, the polymer-PEO 4000-Heparin surface maintained the highest bio-activity. See, K. D. Park et al., supra. Thus, methods are available in the art for controlling the activity of a polymer-bound bio-active agent. By utilizing such methods, one may determine the optimal length of the spacer. Accordingly, as used herein, "effective distance" means the distance between the bound bio-active agent and the polymer backbone which corresponds to a desired level of activity in the bio-active agent.

Thus, in the present invention, control over the bio-active agent's activity is achieved by varying the length, i.e., molecular weight, of the spacer group in Inventive Embodiment I. The spacer group may have a molecular weight of about 100 to about 200,000 daltons. Preferably, the spacer group has a molecular weight of about 200 to about 50,000 daltons. More preferably, the spacer group has a molecular weight of about 1,000 to about 4,000 daltons. Furthermore, the amount of the bio-active agent incorporated can also be controlled by the amount of the $\alpha,\beta$-unsaturated carbonyl groups incorporated in the backbone polymer.

In accordance with the present invention, a significant reduction of thrombus formation and/or infection associated with the use of bio-compatible polymer backbones is achieved by combining an anti-thrombogenic and/or anti-infective agent in a coating to be applied to a host-contacting surface(s) of, for example, a medical device. A variety of anti-infective agents as known in the art may be used, including, antibiotics, such as penicillin and antibacterial agents such as silver sulfadiazine. Similarly, a variety of anti-thrombogenic agents known in the art may be used, including, heparin, hirudin, prostaglandin, urokinase, streptokinase, sulfated polysaccharide, and albumin. In some cases it may be desirable to provide either dual anti-infective or anti-thrombogenic action with two or more agents. Additionally, it may be desirable to combine an anti-infective and an anti-thrombogenic action by combining two or more of these different agents. The invention will be described in terms of the preferred heparin, a known anti-thrombogenic agent of known safety and high anti-coagulation activity, with the understanding that the invention contemplates any anti-thrombogenic and/or anti-infective agent which may be grafted to the polymeric substrate by the method of the present invention.

As described hereinabove, the bio-active coatings of the present invention are designed to be applied to the surface of host-contacting substrates, such as for example, a medical device. A medical device of the present invention may be any polymeric substrate compatible with one of the present bio-active coatings which, absent the coating, may lead to thrombus formation and/or infection when in contact with a body tissue or fluid. The polymeric substrate is preferably made from hydrophobic, inert polymeric material including, for example, polytetrafluoroethylene (ePTFE) and polyethyleneterephthalate (PET). Exemplary of, but not limited to, such medical devices are vascular access (arterial and venous) catheters, introducers, vascular grafts, endoprostheses, stents, stent-graft combinations, urinary catheters and associated substrates, such as drainage bags and connectors, and all abdominal cavity drainage tubing, bags and connectors. Preferred medical devices are, for example, ePTFE vascular grafts. For purposes of this invention, "vascular grafts" is meant to include endoprostheses.

In another embodiment of the present invention, a bio-active coating was prepared in a two-step reaction which is substantially identical to reactions described in RM#4 and RM #5. The first reaction includes reacting a bio-compatible polymer backbone having $\alpha,\beta$-unsaturated carbonyl functionality (VI) with a hydrophilic spacer having at least one reactive functional group at its first and second ends (VII) as shown in RM #4. In this reaction, one of the reactive functional groups of the spacer reacts with a $\beta$-carbon of the carbonyl functionality to bond the spacer to the polymer backbone.

The second reaction, as indicated in RM #5, includes reacting a bio-active agent as described previously with a remaining unreacted functional group of the spacer in the presence of an optional catalyst to covalently bind the bio-active agent to the spacer.

In another embodiment of the invention, a coating composition is provided which is defined by a bio-compatible polymeric backbone having a carbonyl functionality and at least one pendant moiety bonded to a $\beta$-carbon of the carbonyl functionality. This pendant moiety is selected from the group consisting of:

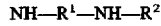

wherein $R^1$ and $R^2$ are a spacer and a bio-active agent, respectively as defined hereinabove.

In a further embodiment of the invention, a method for preparing a bio-active polymer coating is described in which a bio-active group is covalently bonded through a hydrophilic spacer group to a polymer backbone. In particular, this method includes providing a polymer backbone having $\alpha,\beta$-unsaturated carbonyl functionality therewithin as described previously. This polymer backbone may be any backbone capable of participating in these reactions. Preferably, the backbone of the present invention is hydrophobic, which will generate a repulsive force against the hydrophilic spacer, which as stated previously, will aide in tethering the spacer away from the backbone to increase the availability of the bio-active agent. A $\beta$-carbon of the carbonyl functionality is then reacted with a hydrophilic spacer as described above wherein the spacer has at least one reactive functional group at its first and second ends. When finished, this reaction leaves the spacer attached as a pendant group off of the backbone. The pendant spacer group is then reacted with a bio-active agent as described above to covalently bond the bio-active agent to the pendant group.

In the present invention, a catalyst which can drive the above-described reaction may be optionally used. A preferred catalyst is 1-(3-dimethylaminopropyl)-3-ethyl carbodiimide hydrochloride, although others are contemplated.

In yet another embodiment of the present invention, there is provided a polymer-bound bio-active composition represented by the following structure:

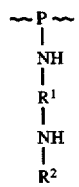

wherein P is a bio-compatible polymer backbone, $R^1$ is a hydrophilic spacer and $R^2$ is a bio-active agent, as described previously.

In a further embodiment of the present invention, a bio-active coating composition includes a polymer backbone having $\alpha,\beta$-unsaturated carbonyl functionality reacted with a hydrophilic spacer having at least one reactive functional group at its first and second ends and a bio-active agent which is covalently reactive with one of the reactive functional groups on the spacer. As used herein, "covalently reactive with" means that the bio-active agent is capable of forming a covalent bond with an unreacted end of the spacer.

EXAMPLE 1

Synthesis of $\alpha,\beta$-Unsaturated Polyurethane Polymer Backbone

A 20% solution of polycarbonate diol (PC diol, molecular weight 890) was made by adding 17.8 gm of PC diol to N,N-dimethyl acetamide (DMAC). A 20% solution of methylene diisocyanate (MDI) was made by adding 7.50 gm MDI to DMAC. A solution of 5% fumaric acid (FA) was made by adding 1.16 gm. FA to DMAC. The MDI solution was taken in a reaction vessel and maintained at 60° C. The PC diol solution was fed into the vessel over 15 minutes and the reaction continued until the desired NCO level was attained (0.134 µm NCO/gm solution). At this time, the fumaric acid solution, containing 0.038 gm dibutyltindiluarate catalyst, was added to the vessel over 15 minutes. This reaction mixture was held at 60° C. for 1 hour. The temperature was then increased to 70° C. for 4 hours. If the reaction mixture becomes viscous, 166 gm of DMAC may be added. The reaction mixture was maintained at 70° C. for an additional 2 hours. The heat was mined off and the reaction mixture was stirred for approximately 14 hours at room temperature. The reaction was then terminated by adding a terminating agent, such as for example 5 mM dibutyl amine (DBA) (0.65 gm in 5.0 gm DMAC) with stirring for 1 hour. Other terminating agents, such as for example, alcohols may also be used.

The polymer composition (hereinafter Composition A) was precipitated out of solution by adding it dropwise into 2.5 L reverse osmosis (RO) water. The precipitate was stirred for three hours in 2.5 L of RO water. The RO water was decanted and the precipitated polymer composition was cut into small pieces and stirred for approximately 14 hours in 1.5 L of RO water. The RO water was decanted and 1.5 L of flesh RO water was added and stirred for approximately 14 hours. The RO water was decanted and 1.0 L of flesh RO water was added and stirred for 2 hours. This procedure was repeated three times total. The RO water was decanted a final time and Composition A was allowed to air dry for approximately 60 hours. Composition A was then dried under vacuum at about 35°–40° C. for approximately 7 hours. Approximately 19.5 gm (dry weight) of Composition A was obtained.

EXAMPLE 2

Synthesis of $\alpha,\beta$-Unsaturated Polyurethane Bound Amine-Terminated PEO

A 5% solution was made of Composition A of Example 1 by adding 3.75 gm of Composition A to 75.0 gm of DMAC. A solution of a previously prepared amine-terminated poly (ethylene)oxide (PEO) (Jeffamine ED2001, molecular weight=2,000) was prepared by adding 30 gm of amine-terminated PEO to 270 gm DMAC.

Composition A and me-terminated PEO was mixed in an Erleumeyer flask in an oil bath at approximately 65° C. with stirring. Twenty-five (25) ml of anhydrous methanol was slowly added to the mixture over the course of 3–4 minutes. The flask was stoppered, maintained under a nitrogen blanket and stirred at 65° C. for 42 hours.

The solution was roto-evaporated to 83 gm. The roto-evaporated solution was then added to ether which caused a brown colored material to precipitate out of the solution. The precipitate was then caused to go back into solution when RO water was added. This solution was placed in a 500 ml Erlenmeyer flask and evaporated to dryness.

250 ml of isopropyl alcohol (IPA) was added to the Erlenmeyer flask and stirred at room temperature for approximately 30 minutes. Thereafter, a gummy, rubbery polymer composition was observed sticking to the flask while the IPA layer remained clear. The IPA layer was decanted and 150 ml of fresh IPA was added to the polymer-containing flask which was then stirred for approximately 30 minutes. The IPA layer was decanted off and 100 ml of fresh IPA was added to the polymer-containing flask and stirred for approximately 30 minutes. The IPA layer was decanted off and replaced with 150 ml RO water. The polymer-containing flask was stirred for 1 hour at room temperature. The polymer was filtered, washed with an additional 100 ml RO water and dried in a vacuum oven at about 35°–40° C. Approximately 3.5 gm of a brown colored rubbery polymer was obtained (hereinafter Composition B).

EXAMPLE 3

Synthesis of $\alpha,\beta$-Unsaturated Polyurethane-Poly (ethylene oxide)-Heparin Approximately 1.5 gm of Composition B, prepared as described in Example 2, was dissolved in 28.5 gm DMAC and 1.0 gm RO water. In addition, a heparin solution was made by dissolving 0.6 Na-heparin (Sigma) in 6.0 gm RO water and then adding 193.4 gm anhydrous DMAC. The solution which contained Composition B was combined with the heparin solution at pH 9.54. The pH of the mixture was adjusted to pH 4.7 by dropwise addition of 1N HCL. A 3% (wt) EDC solution containing 0.096 gm EDC, 3.0 gm DMAC and 0.1 gm RO water was added to the Composition B-heparin mixture in 6 installments approximately every 30 minutes over 2.5 hours. After the first half hour, the pH of the mixture was raised to 7.62 by dropwise addition of 1N NaOH. After the EDC solution was completely added to the Composition B-heparin mixture, it was stirred for approximately 14 hours at room temperature.

The mixture was then roto-evaporated to 48.0 gm and then precipitated in 500 ml ether. The ether was decanted and 500 ml of RO water was added. The polymer was filtered and the water layer was centrifuged. The polymer pellet was washed with water and then combined with the filtered polymer material. All of the polymer material was transferred to a Teflon dish and was dried under vacuum at about 35°–40° C. Approximately 1.17 gm of the heparin bound polymer was obtained (hereinafter Compound C).

The invention being thus described, it will be obvious that the same may be varied in many ways. Such variations are not to be regarded as a departure from the spirit and scope of the invention and all such modifications are intended to be included within the scope of the following claims.

What is claimed is:

1. A bio-active coating comprising the reaction product of:
   a) a first reaction that includes reacting a bio-compatible polymer backbone having $\alpha,\beta$-unsaturated carbonyl functionality with a hydrophilic spacer having at least one reactive functional group at its first and second ends, wherein one of said reactive functional groups reacts with a $\beta$-carbon of said unsaturated carbonyl functionality to bond said spacer to said polymer backbone; and
   b) a second reaction that includes reacting a bio-active agent with a remaining unreacted reactive functional group of said spacer to covalently bind said bio-active agent to said spacer.

2. The bio-active coating of claim 1, wherein said polymer backbone is a polyurethane selected from the group consisting of polyesterurethaneureas, polyetherurethaneureas, polycarbonateurethaneureas and mixtures thereof.

3. The bio-active coating of claim 1, wherein said hydrophilic spacer is selected from the group consisting of hydrophilic aliphatic hydrocarbons, poly(oxy olefins) hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides.

4. The bio-active coating of claim 1, wherein said hydrophilic spacer is an amino terminated poly(ethylene oxide).

5. The bio-active coating of claim 1, wherein said reactive functional group of said spacer is selected from the group consisting of amino, carboxyl, isocyanate, hydroxyl and mixtures thereof.

6. The bio-active coating of claim 4, wherein said amino terminated poly(ethylene oxide) has a molecular weight of about 100 daltons to about 200,000 daltons.

7. The bio-active coating of claim 4, wherein said amino terminated poly(ethylene oxide) has a molecular weight of about 200 to about 50,000 daltons.

8. The bio-active coating of claim 4, wherein said amino terminated poly(ethylene oxide) has a molecular weight of about 1,000 to about 4,000 daltons.

9. The bio-active coating of claim 1, wherein the molecular weight of said hydrophilic spacer positions said bioactive agent at a bio-effective distance from said polymer backbone.

10. The bio-active coating of claim 1, wherein said bio-active agent is selected from the group consisting of anti-thrombogenic agents, antibiotic agents, antiviral agents, their pharmaceutical salts and mixtures thereof.

11. The bio-active coating of claim 1, wherein said bio-active agent is heparin, an aldehyde-terminated heparin and pharmaceutical salts thereof.

12. The bio-active coating of claim 1, wherein said second reaction occurs in the presence of a catalyst.

13. The bio-active coating of claim 12, wherein said catalyst is 1-(3-dimethylaminopropyl)-3-ethylcarbodiimide hydrochloride.

14. The bio-active coating of claim 1, wherein said first reaction is carried out in the presence of an acid.

15. A coating composition including a polymeric structure defined by a bio-compatible polymeric backbone having $\alpha,\beta$-unsaturated carbonyl functionality and at least one pendant moiety bonded to a $\beta$-carbon of said unsaturated carbonyl functionality, said pendant moiety selected from the group consisting of:

$$NH-R^1-NH-R^2,$$

wherein $R^1$ is a hydrophilic spacer group selected from the group consisting of aliphatic hydrocarbons, poly(oxy olfins), hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides; and $R^2$ is a bio-active agent selected from the group consisting of antithrombogenic agents, antibiotics, antibacterial agents, antiviral agents, their pharmaceutical salts and mixtures thereof.

16. A coating composition of claim 15, wherein said hydrophilic spacer group is a residue of an amino terminated poly(ethylene oxide).

17. A coating composition of claim 16, wherein said amino terminated poly(ethylene oxide) has a molecular weight of about 100 daltons to about 200,000 daltons.

18. A coating composition of claim 16, wherein said amino terminated poly(ethylene oxide) has a molecular weight of about 200 to about 50,000 daltons.

19. A coating composition of claim 16, wherein said amino terminated poly(ethylene oxide) has a molecular weight of about 1,000 to about 4,000 daltons.

20. A coating composition of claim 15, wherein the molecular weight of said spacer positions said bio-active agent at a bio-effective distance from said polymer backbone.

21. A coating composition of claim 15, wherein said antithrombogenic agent is heparin, an aldehyde-terminated heparin and its pharmaceutical salts.

22. A coating composition of claim 15, wherein said polymeric backbone is a polyurethane selected from the group consisting of polyetherurethaneureas, polyesterurethaneureas, polycarbonateurethaneureas and mixtures thereof.

23. A method for preparing a bio-active polymer coating having a bio-active group covalently bonded through a hydrophilic spacer group to a polymer backbone comprising:
   a) providing a polymer backbone having $\alpha,\beta$-unsaturated carbonyl functionality therewithin;
   b) reacting a $\beta$-carbon of said unsaturated carbonyl functionality with said hydrophilic spacer having at least one reactive functional group at its first and second ends to attach said hydrophilic spacer as a pendant group off said backbone; and
   d) further reacting said pendant group with a bio-active agent to covalently bond said bio-active agent to said pendant group.

24. The method of claim 23, wherein said hydrophilic spacer is selected from the group consisting of aliphatic hydrocarbons, poly(oxy olefins) hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides.

25. The method of claim 23, wherein said hydrophilic spacer is an amino terminated poly(ethylene oxide).

26. The method of claim 25, wherein said amino terminated poly(ethylene oxide) has a molecular weight of about 100 daltons to about 200,000 daltons.

27. The method of claim 25, wherein said amino terminated poly(ethylene oxide) has a molecular weight of about 200 to about 50,000 daltons.

28. The method of claim 25, wherein said amino terminated poly(ethylene oxide) has a molecular weight of about 1,000 to about 4,000 daltons.

29. The method of claim 23, wherein the molecular weight of said hydrophilic spacer positions said bio-active agent at a bio-effective distance from said polymer backbone.

30. The method of claim 23, wherein said bio-active agent is selected from the group consisting of anti-thrombogenic agents, antibiotic agents, antibacterial agents, antiviral agents, their pharmaceutical salts, and mixtures thereof.

31. The method of claim 23, wherein said bio-active agent is heparin, an aldehyde-terminated heparin and pharmaceutical salts thereof.

32. The method of claim 23, wherein said further reacting occurs in the presence of a catalyst.

33. The method of claim 32, wherein said catalyst is 1-(3-dimethylaminopropyl)-3-ethylcarbodiimide hydrochloride.

34. The method of claim 23, wherein said polymer backbone is a polyurethane selected from the group consisting of polyesterurethaneureas, polyetherurethaneureas, polycarbonateurethaneureas and mixtures thereof.

35. A polymer-bound bio-active composition represented by the structure:

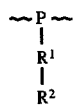

wherein P is a biocompatible polymer backbone having a β-carbonyl derived from an α,β-unsaturated carbonyl functionality therewithin; $R^1$ is a hydrophilic spacer group having at least one reactive functional group at its first and second ends and is further selected from the group consisting of aliphatic hydrocarbons, poly(oxy olefins) hydrophilic polyethers, hydrophilic polyethylenes, modified polyolefins, aliphatic polyesters, polyamines, polysiloxanes, polysilazanes, hydrophilic acrylates, hydrophilic methacrylates, polyamino acids, and linear polysaccharides; and $R^2$ is a bio-active agent selected from the group consisting of antithrombogenic agents, antibiotics, antibacterial agents, antiviral agents, their pharmaceutical salts and mixtures thereof.

36. The bio-active coating of claim 35, wherein said polymer backbone is a polyurethane selected from the group consisting of polyetherurethaneureas, polyesterurethaneureas, polycarbonateurethaneureas and mixtures thereof.

37. The bio-active coating of claim 35, wherein said reactive functional group of said spacer is selected from the group consisting of hydroxyl, amino, carboxyl, isocyanate, and mixtures thereof.

38. The bio-active coating of claim 35, wherein said spacer is an amino terminated poly(ethylene oxide).

39. The bio-active coating of claim 38, wherein said amino terminated poly(ethylene oxide) has a molecular weight of about 100 daltons to about 200,000 daltons.

40. The bio-active coating of claim 38, wherein said amino terminated poly(ethylene oxide) has a molecular weight of about 200 to about 50,000 daltons.

41. The bio-active coating of claim 38, wherein said amino terminated poly(ethylene oxide) has a molecular weight of about 1,000 to about 4,000 daltons.

42. The bio-active coating of claim 35, wherein the molecular weight of said spacer positions said bio-active agent at a bio-effective distance from said polymer backbone.

43. The bio-active coating of claim 35, wherein said bio-active agent is heparin, an aldehyde-terminated heparin and pharmaceutical salts thereof.

44. A bio-active coating composition comprising a polymer backbone having at least one pendant moiety bonded to a β-carbon of an α,β-unsaturated functionality, said composition prepared by the process of:

a) reacting a poly(diol) with methylene diisocyanate to form a NCO-terminated prepolymer;

b) reacting a compound having an α,β-unsaturated carbonyl functionality with said NCO terminated prepolymer to form said polymer backbone;

c) reacting said polymer backbone with a hydrophilic spacer group having at least one reactive functionality at its first and second ends; and d) reacting a bio-active agent with an unreacted end of said hydrophilic spacer to convalently bond said bio-active agent to said polymer backbone via said hydrophilic spacer.

* * * * *

UNITED STATES PATENT AND TRADEMARK OFFICE
CERTIFICATE OF CORRECTION

PATENT NO. : 5,741,881
DATED : April 21, 1998
INVENTOR(S) : Birendra K. Patnaik

It is certified that error appears in the above-identified patent and that said Letters Patent is hereby corrected as shown below:

Column 5, Line 41,      now reads "hydropbilic polyethylenes", should read --hydrophilic polyethylenes--, Column 6, Line 11,      now reads "polyarethanes", should read --polyurethanes--;

Column 11, Line 67,      now reads "L of flesh RO water", should read --L of fresh RO water;

IN THE CLAIMS

Claim 44, Column 16, Line 37      now reads "unsaturated functionality", should read -- unsaturated carbonyl functionality--.

Signed and Sealed this

Fifth Day of January, 1999

Attest:

Attesting Officer

*Acting Commissioner of Patents and Trademarks*